(12) United States Patent
Luu et al.

(10) Patent No.: US 7,235,700 B2
(45) Date of Patent: Jun. 26, 2007

(54) PROCESS FOR PRODUCING CYCLOHEXENONE LONG-CHAIN ALCOHOLS

(75) Inventors: Bang Luu, Strasbourg (FR); Patrick Neuberg, Strasbourg (FR); Delphine Trancard, Strasbourg (FR); Masashi Yamada, Tokyo (JP); Yukio Ohshiba, Odawara (JP); Hiroto Suzuki, Tokyo (JP)

(73) Assignee: Meiji Dairies Corporation, Tokyo (JP)

( * ) Notice: Subject to any disclaimer, the term of this patent is extended or adjusted under 35 U.S.C. 154(b) by 127 days.

(21) Appl. No.: 10/550,305

(22) PCT Filed: Mar. 28, 2003

(86) PCT No.: PCT/JP03/03994

§ 371 (c)(1),
(2), (4) Date: Sep. 22, 2005

(87) PCT Pub. No.: WO2004/087630

PCT Pub. Date: Oct. 14, 2004

(65) Prior Publication Data

US 2006/0135818 A1    Jun. 22, 2006

(51) Int. Cl.
*C07C 45/00* (2006.01)

(52) U.S. Cl. ..................... 568/343; 568/347

(58) Field of Classification Search ............. None
See application file for complete search history.

(56) References Cited

U.S. PATENT DOCUMENTS

| | | | | |
|---|---|---|---|---|
| 6,228,893 | B1 | 5/2001 | Luu et al. | 514/690 |
| 6,906,107 | B2 * | 6/2005 | Miyagawa et al. | 514/690 |
| 2004/0102527 | A1 | 5/2004 | Miyagawa et al. | 514/690 |
| 2004/0115810 | A1 | 6/2004 | Luu et al. | 435/441 |
| 2004/0152786 | A1 | 8/2004 | Luu et al. | 514/690 |

FOREIGN PATENT DOCUMENTS

| | | |
|---|---|---|
| JP | 2001-089404 | 4/2001 |
| JP | 2001-515058 | 9/2001 |
| JP | 2003-212811 | 7/2003 |
| WO | 00 47199 | 8/2000 |

OTHER PUBLICATIONS

Cossy et al. Reactivity of Tris(Trimethylsilyl)sily Radical with Beta-Alkenyloxyenones. Tetrahedron Letters, 1995, vol. 36 (40), p. 7235-7238.*
Mori, Kenji et al, "Synthesis of sphingosine relatives, X. Synthesis of (2S,3R, 4E)-1-0-(.beta.-D-glucopyranosyl)-N-'30'-(linoleoyloxy)triacontanoyl!-4-icosasphing enine, a new esterified cerebroside isolated from human and pig epidermis", Liebigs Annalen Der Chemie, vol. 6, p. 530, XP002262862, 1991.
U.S. Appl. No. 10/550,305, filed Sep. 22, 2005, Luu et al.
U.S. Appl. No. 09/890,969, filed Apr. 11, 2002, Luu et al.

* cited by examiner

*Primary Examiner*—Sikarl A. Witherspoon
(74) *Attorney, Agent, or Firm*—Oblon, Spivak, McClelland, Maier & Neustadt, P.C.

(57) ABSTRACT

A process for producing cyclohexenone long-chain alcohol represented by the following formula (1): (wherein A represents a C10-C18 alkylene or alkenylene group, and each of $R^1$, $R^2$, and $R^3$ individually represents hydrogen or methyl), comprising reacting a 3-alkoxy-2-cyclohexen-1-one derivative represented by the following formula (2): (wherein $R^1$, $R^2$, and $R^3$ have the same meanings as above, and $R^4$ represents a C1-C5 alkyl group) with a Grignard's reagent prepared by protecting the hydroxyl groups of C10-C18 ω-halogenoalcohol through silylation, and hydrolyzing the resultant reaction product. The process of the present invention for producing cyclohexenone long-chain alcohol requires a reduced number of reaction steps, can be performed with ease and with reduced production cost, and thus finds utility in the industry

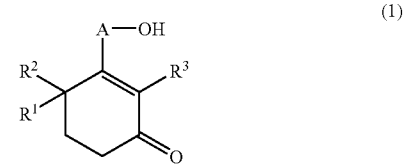 (1)

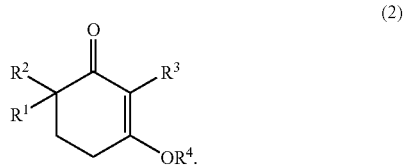

(2)

1 Claim, No Drawings

PROCESS FOR PRODUCING CYCLOHEXENONE LONG-CHAIN ALCOHOLS

TECHNICAL FIELD

The present invention relates to a process for producing a cyclohexenone long-chain alcohol, which process requires a reduced number of reaction steps and can be performed with ease and is thus industrially advantageous.

BACKGROUND ART

Nerve growth factor (NGF), which is found in particular abundance in the hippocampus and cerebral cortex of the brain, is a neurotrophic factor which is required by a living body for sustaining life and functions and stimulates differentiation and growth of neurons. In the brain, NGF acts on cholinergic neurons. Alzheimer's disease is accepted to exhibit a primary lesion of regeneration and falling of cholinergic neurons, and on the basis of this understanding, NGF has been administered to the brain as therapy for the disease.

However, NGF, being a protein having a molecular weight of 12,000, cannot pass through the blood-brain barrier, and thus does not serve as practical means for the treatment of Alzheimer's disease.

Meanwhile, cyclohexenone long-chain alcohol has a low molecular weight and is known to be useful as a prophylactic or therapeutic drug for cerebral diseases such as dementia, in view that, when administered orally, the alcohol reaches the brain, passes through the blood-brain barrier, and at low concentration exhibits excellent effect to stimulate growth of neurons, to thereby directly act on neurites to elicit extension (Japanese Kohyo (PCT) Patent Publication No. 2001-515058).

Hitherto, cyclohexenone long-chain alcohol has been produced through a complicated process; for example, by reacting cyclohexanone or methyl-substituted 2-cyclohexen-1-one with benzenesulfinate in the presence of acid, then with ethylene glycol to form a ketal compound, and further with ω-halogenoalcanol, followed by treatment with an acid to remove a protective group. Specifically, in the case of production of 3-(14-hydroxytetradecyl)-4-methyl-2-cyclohexen-1-one from a starting material 3-methylcyclohexenone, seven reaction steps have conventionally been required.

DISCLOSURE OF THE INVENTION

As described above, the conventional process for producing cyclohexenone long-chain alcohol requires a number of complicated and intricate steps, involves high production cost, and is thus industrially disadvantageous.

Accordingly, an object of the present invention is to provide an industrially advantageous process for producing cyclohexenone long-chain alcohol, which process requires a reduced number of reaction steps and can be performed with ease and at reduced production cost.

The present inventors have performed extensive studies for developing a simple, convenient process for producing cyclohexenone long-chain alcohol starting from a known substance, and have found that when cyclohexenone of enol form—which can be produced with ease from a known substance 1,3-cyclohexanedione—is subjected to Grignard reaction by use of ω-halogeno long-chain alcohol whose hydroxyl group is protected through silylation, cyclohexenone long-chain alcohol can be obtained through a reduced number of steps, conveniently, at low production cost, and in an industrially advantageous manner, thus leading to completion of the invention.

Accordingly, the present invention provides a process for producing cyclohexenone long-chain alcohol represented by the following formula (1):

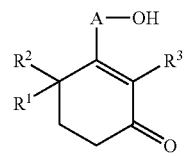

(1)

(wherein A represents a C10-C18 alkylene or alkenylene group, and each of $R^1$, $R^2$, and $R^3$ individually represents a hydrogen atom or a methyl group), comprising reacting a 3-alkoxy-2-cyclohexen-1-one derivative represented by the following formula (2):

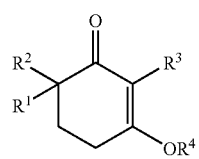

(2)

(wherein $R^1$, $R^2$, and $R^3$ have the same meanings as above, and $R^4$ represents a C1-C5 alkyl group) with a Grignard's reagent prepared from C10-C18 ω-halogenoalcohol whose hydroxyl group is protected through silylation, and hydrolyzing the resultant reaction product.

DETAILED DESCRIPTION OF THE PREFERRED EMBODIMENTS

In the starting compound represented by formula (2) (hereinafter referred to as compound (2)), each of $R^1$, $R^2$, and $R^3$ represents a hydrogen atom. Preferably, at least one of these is methyl. The following cases are particularly preferred: $R^1=CH_3$ and $R^2=R^3=H$, or $R^1=R^2=R^3=CH_3$. $R^4$ represents a C1-C5 alkyl, with ethyl being particularly preferred.

Examples of preferred starting compound (2) include 3-ethoxy-6-methyl-2-cyclohexen-1-one, 3-ethoxy-2,6-dimethyl-2-cyclohexen-1-one, and 3-methoxy-2,6,6-trimethyl-2-cyclohexen-1-one.

The starting compound (2) can be obtained through enolation and methylation of 1,3-cyclohexanedione, which is available at low cost. The sequence in which enolation and methylation are carried out is not critical, and enolation may precede methylation or vice versa. When all of $R^1$, $R^2$, and $R^3$ are hydrogen atoms, methylation is not necessary.

Enolation may be performed by reacting 1,3-cyclohexanedione, which may optionally be methylated if necessary (e.g., 2-methyl-1,3-cyclohexanedione), with alcohol ($R^4OH$) in the presence of an acid catalyst. Examples of the acid catalyst include p-toluenesulfonic acid and sulfuric acid. The reaction is carried out in a solvent such as toluene, xylene, methanol, or ethanol, at 60-150° C. for 2 to 10 hours.

Methylation is performed by, for example, reacting enolated 1,3-cyclohexanedione, which may optionally be enolated if necessary, with a lithiation reagent such as lithium diisopropylamide obtained through reaction between alkyl lithium and diisopropylamine, then with a methylation agent such as methyl iodide. The lithiation reaction is preferably performed by cooling a solution prepared by adding lithium diisopropylamine to tetrahydrofuran or hexane to −80 to 0° C. (e.g., −78° C.), then adding optionally enolated 1,3-cyclohexanedione (preferably 3-ethoxy-2-cyclohexan-1-one) dissolved in tetrahydrofuran, hexane, etc. Preferably, methylation is performed after adding methyl iodide to the resultant reaction mixture and heating the mixture to 5 to 30° C. (e.g., room temperature), while stirring the mixture for 5 to 12 hours.

The thus-obtained compound (2) is reacted with a Grignard's reagent prepared from C10-C18 ω-halogenoalcanol whose hydroxy group is protected through silylation, and is then subjected to hydrolysis, to thereby produce a cyclohexenone long-chain alcohol (1). Examples of the C10-C18 ω-halogenoalcanol which has undergone silylation include the compound represented by the following formula (3):

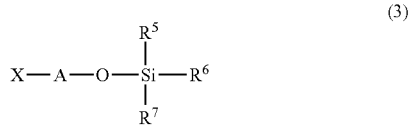

(3)

(wherein X represents a halogen atom, A represents a C10-C18 alkylene or alkenylene group, and each of $R^5$, $R^6$, and $R^7$ represents a C1-C8 alkyl group). Examples of X include Cl, Br, and I, with Br being preferred. Examples of A include C10-C18 linear or branched alkylene or alkenylene groups, with C12-C16 linear or branched alkylene groups being more preferred, and C12-C16 linear alkylene groups being even more preferred, and tetradecylene and pentadecylene being most preferred. Examples of $R^5$, $R^6$, and $R^7$ include a methyl group, an ethyl group, an isopropyl group, and a t-butyl group.

The Grignard's reagent used in the present invention can be obtained by a conventional method, through reaction between a silylated ω-halogenoalcanol and magnesium.

The reaction between the compound (2) and the Grignard's reagent is performed in the manner of an ordinary Grignard reaction, and preferably in an absolute solvent such as diethyl ether or tetrahydrofuran at 40-80° C. for 0.5 to 3 hours.

The subsequent hydrolysis is preferably performed in the presence of an acid such as p-toluenesulfonic acid, hydrochloric acid, or sulfuric acid. Through hydrolysis, the group $R^4$, the Grignard's reagent, and the silylation-protective group are removed.

In each reaction step of the process of the present invention, the resultant intermediate may be isolated and then forwarded to the next reaction step. However, the intermediate may be forwarded directly to the next reaction step, without being isolated. In the present invention, the intermediate or a target compound can be isolated from a reaction mixture through washing, extraction, recrystallization, chromatographic techniques, etc., solely or in combination.

EXAMPLES

The present invention will next be described by way of Examples, which should not be construed as limiting the invention thereto.

Example 1

Synthesis of 3-(15-hydroxypentadecyl)-2,4,4-trimethyl-2-cyclohexen-1-one (1) Synthesis of 3-ethoxy-2-methyl-2-cyclohexen-1-one 2-Methyl-1,3-cyclohexanedione (3 g, 23.8 mmol) was dissolved in a mixture of ethanol (30 mL) and toluene (56 mL), and to the resultant mixture, p-toluenesulfonic acid (92 mg, 0.47 mmol) was added. The mixture was allowed to react while refluxing with heat. Subsequently, the water/ethanol/toluene azeotrope (boiling point: 78° C.) was distilled off, and the remaining toluene was removed under reduced pressure. The crude product was purified by silica gel flash chromatography (ethyl ether/hexane=8/2), to thereby yield 2.7 g (17.4 mmol) of 3-ethoxy-2-methyl-2-cyclohexen-1-one.
Yield: 73%
$R_f$ (ethyl ether/hexane=80/20)=0.37
$^1$H-NMR(200 MHz, CDCl$_3$) δ: 1.32(t, $^3$J=7.00 Hz, 3H, H-9), 1.67(t, $^4$J=1.49 Hz, 3H, H-7), 1.94(qn, $^3$J=6.33 Hz, 2H, H-5), 2.31(t, $^3$J=6.62 Hz, 2H, H-6), 2.51(td, $^3$J=6.12 Hz, $^4$J=1.44 Hz, 2H, H-4), 4.03(q, $^3$J=7.00 Hz, 2H, H-8).
$^{13}$C-NMR(50 MHz, CDCl$_3$) δ: 7.4(C-7), 15.4(C-9), 21.1 (C-5), 25.4(C-4), 36.4(C-6), 63.5(C-8), 115.1(C-2), 171.4 (C-3), 198.9(C-1).

(2) Synthesis of 3-ethoxy-2,6-dimethyl-2-cyclohexen-1-one:

Diisopropylamine (2.35 mL, 19.45 mmol) dissolved in tetrahydrofuran (8 mL) was cooled to −78° C., n-butyllithium (12.96 mL, 19.45 mmol) was added thereto, and the temperature was elevated to 0° C. After having been stirred for 2 hours at 0° C., the reaction mixture was cooled to −78° C., and 3-ethoxy-2-methyl-2-cyclohexen-1-one (2 g, 12.96 mmol) dissolved in tetrahydrofuran (5 mL) was added thereto. One hour later, methyl iodide (1.21 mL, 19.45 mmol) was added thereto, and the temperature of the reaction mixture was allowed to rise to room temperature. The reaction mixture was stirred overnight, diluted with water (100 mL), and then extracted three times with ethyl ether. The organic layers were combined, washed with an aqueous NaCl solution, dried over magnesium sulfate, filtered, and concentrated under reduced pressure. The crude product was applied to silica, and purified by means of silica gel column chromatography (ethyl ether/hexane=4/6), to thereby yield 1.72 g (10.24 mmol) of 3-ethoxy-2,6-dimethyl-2-cyclohexen-1-one.
Yield: 79%
$R_f$ (ethyl ether/hexane=40/60)=0.9
$^1$H-NMR(200 MHz, CDCl$_3$) δ: 1.12(d, 3H, H-8), 1.33(t, $^3$=7.00 Hz, 3H, H-10), 1.5 4-1.74(m, 4H, H-5, H-7), 1.98-2.11(m, 1H, H-5'), 2.19-2.31(m, 1H, H-6), 2.51-2.6 0(m, 2H, H-4), 4.04(qd, J=4.68 Hz, J=2.33 Hz, 2H, H-9).
$^{13}$C-NMR(50 MHz, CDCl$_3$) δ: 7.4(C-7), 15.3 and 15.7 (C-8, C-10), 24.5(C-5), 28.9(C-4), 39.5(C-6), 63.3(C-9), 114.3(C-2), 170.2(C-3), 201.2(C-1).

(3) Synthesis of 3-ethoxy-2,6,6-trimethyl-2-cyclohexen-1-one

Diisopropylamine (1.45 mL, 10.34 mmol) dissolved in tetrahydrofuran (3 mL) was cooled to −78° C., n-butyllithium (8.7 mL, 10.46 mmol) was added thereto, and the temperature was elevated to 0° C. After having been stirred for 2 hours at 0° C., the reaction mixture was cooled to −78° C., and 3-ethoxy-2,6-dimethyl-2-cyclohexen-1-one (1.47 g, 8.72 mmol) dissolved in tetrahydrofuran (6 mL) was added thereto. One hour later, methyl iodide (1.59 mL, 10.46 mmol) was added thereto, and the temperature of the reaction mixture was allowed to rise to room temperature. The reaction mixture was stirred overnight, diluted with water (100 mL), and then extracted three times with ethyl ether. The organic layers were combined, washed with an aqueous NaCl solution, dried over magnesium sulfate, filtered, and concentrated under reduced pressure. The crude product was purified by silica gel column chromatography (ethyl ether/hexane=4/6), to thereby yield 1.46 g (8.04 mmol) of 3-ethoxy-2,6,6-trimethyl-2-cyclohexen-1-one.

Yield: 92.2%

$R_f$(ethyl ether/hexane=40/60)=0.31

$^1$H-NMR(200 MHz, CDCl$_3$) δ: 1.03(s, 6H, H-8, H-9), 1.30(t, $^3$J=7.01 Hz, 3H-11), 1.64 (t, $^4$J=1.6 Hz, 3H, H-7), 1.75(t, $^3$J=6.27 Hz, 2H, H-5), 2.51(tq, $^3$J=6.29 Hz, $^4$J=1.5 6 Hz, 2H, H-4), 4.01(q, $^3$J=6.97 Hz, 2H, H-10).

$^{13}$C-NMR(50 MHz, CDCl$_3$) δ: 8.0(C-7), 15.4(C-11), 22.6 (C-4), 24.7(C-8, C-9), 34.7(C-5), 39.5(C-6), 63.2(C-10), 113.1(C-2), 169.0(C-3), 203.6(C-1).

(4) Synthesis of 15-bromo-1-(t-butyldimethylsiloxy)-pentadecane (a) Synthesis of 1,15-pentadecanediol Pentadecanolide (5 g, 20.8 mmol) dissolved in tetrahydrofuran (150 mL) was cooled to 0° C., and to the resultant solution, aluminum lithium hydride (1.2 g, 31.2 mmol) was added in portions. The temperature of the mixture was then returned to room temperature. The reaction mixture was stirred for three days at room temperature, and subsequently, an aqueous saturated tartaric acid solution (200 mL) was added thereto at 0° C. The mixture was subjected to extraction with ethyl ether three times. The organic layers were combined, washed with aqueous sodium chloride solution, dried over magnesium sulfate, filtered, and concentrated under reduced pressure, to thereby yield 5.01 g (20.5 mmol) of 1,15-pentadecanediol.

Yield: 98.6%

$R_f$(hexane/ethyl acetate=10/90)=0.44

Melting point: 84-85° C.

$^1$H-NMR(200 MHz, CDCl$_3$) δ: 1.28(s large, 22H, H-3 to H-13), 1.56(qn, $^3$J=6.6 Hz, 4H, H-2, 14), 3.64(t, $^3$J=6.6 Hz, 4H, H-1, 15).

$^{13}$C-NMR(50 MHz, CDCl$_3$) δ: 26.5(C-3, 13), 29.9(C-4 to C-12), 33.7(C-2, C-14), 62.1(C-1, 15).

(b) Synthesis of 15-bromo-pentadecan-1-ol

48% Hydrogen bromide (50 mL) was gradually added to a mixture of 1,15-pentadecanediol (5.08 g, 20.8 mmol) and cyclohexane (50 mL), and the resultant mixture was refluxed with heat for 6 hours, followed by separation into two layers. The aqueous layer was subjected to extraction with hexane three times. The organic layers were combined, washed with aqueous saturated sodium hydrogencarbonate solution and aqueous sodium chloride solution, dried over magnesium sulfate, and concentrated under reduced pressure. The crude product was applied to silica for purification by means of silica gel column chromatography (hexane/ethyl acetate=7/3), to thereby yield 4.33 g (14.08 mmol) of 15-bromo-pentadecan-1-ol.

Yield: 68%

$R_f$(hexane/ethyl acetate=60/40)=0.47

Melting point: 61-63° C.

$^1$H-NMR(200 MHz, CDCl$_3$) δ: 1.28(s large, 22H, H-3 to H-13), 1.57(qn, $^3$J=6.7 Hz, 2H, H-2), 1.86(qn, $^3$J=6.8 Hz, 2H, H-14), 3.41(t,$^3$J=6.8 Hz, 2H, H-15), 3.65(t, $^3$J=6.6 Hz, 2H, H-1).

$^{13}$C-NMR(50 MHz, CDCl$_3$) δ: 25.5(C-3), 28.1(C-13), 28.5(C-12), 29.4(C-4 to C-11), 32.7(C-2,C-15), 33.8(C-14), 62.9(C-1).

(c) Synthesis of 15-bromo-1-(t-butyldimethylsiloxy)-pentadecane

15-Bromo-pentadecan-1-ol (2.3 g, 7.49 mmol) dissolved in methylene chloride (23 mL) was mixed with trimethylamine (2.1 mL, 14.98 mmol), t-butyldimethylsilyl chloride (2.03 g, 13.48 mmol), and dimethylaminopyridine (457.6 mg, 3.74 mmol). The mixture was stirred for one hour at room temperature. Subsequently, aqueous saturated ammonium chloride solution was added to the reaction mixture for separation into a methylene chloride layer (200 mL) and an aqueous layer (200 mL). The organic layer was dried over magnesium sulfate, filtered, and concentrated under reduced pressure. The crude product was purified by means of silica gel column flash chromatography (hexane/ethyl acetate=99/1), to thereby afford 2.98 g (7.07 mmol) of 15-bromo-1-(t-butyldimethylsiloxy)pentadecane.

Yield: 94.4%

$R_f$(hexane=100)=0.43

$^1$H-NMR(200 MHz, CDCl$_3$) δ: 0.00(s, 6H, Me), 0.85(s, 9H, tBu), 1.21(s large, 22H, H-3 to H-13), 1.33-1.46(m, 2H, H-2), 1.74-1.88(m, 2H, H-14), 3.36(t, $^3$J=6.89 Hz, 2H, H-15), 3.55(t, $^3$J=6.52 Hz, 2H, H-1).

$^{13}$C-NMR(50 MHz, CDCl$_3$) δ: −5.2(Me), 26(tBu), 28.2-29.7(C-3 to C-13), 33(C-15), 35(C-2, C-14), 63(C-1).

(5) Synthesis of 3-(15-hydroxypentadecyl)-2,4,4-trimethyl-2-cyclohexen-1-one

15-Bromo-1-(t-butyldimethylsiloxy)pentadecane (1 g, 2.36 mmol) dissolved in absolute ethyl ether (3 mL) and magnesium (0.115 g) were mixed, and the mixture was refluxed for 40 minutes. Subsequently, 3-ethoxy-2,6,6-trimethyl-2-cyclohexen-1-one (287.5 mg, 1.57 mmol) dissolved in tetrahydrofuran (2 mL) was added thereto. After stirring the mixture for four hours, 10% hydrochloric acid (3 mL) was added, and the reaction was allowed to continue for a further 17 hours under stirring. The reaction mixture was neutralized with sodium hydrogencarbonate, followed by extraction with ethyl ether three times. The organic layers were combined, washed with aqueous sodium chloride solution, dried over magnesium sulfate, filtered, and concentrated under reduced pressure. The crude product was purified by means of silica gel column chromatography (hexane/ethyl acetate=9/1-6/4; concentration gradient=5%), to thereby afford 222.7 mg (0.61 mmol) of 3-(15-hydroxypentadecyl)-2,4,4-trimethyl-2-cyclohexen-1-one.

Yield: 39%

$R_f$(hexane/ethyl acetate=70/30)=0.26

Melting point: 29-30° C.

$^1$H-NMR(200 MHz, CDCl$_3$) δ: 1.06(s, 6H, H-22, 23), 1.17(m, 24H, H-8 a H-19), 1.47 (m, 2H, H-20), 1.68(s, 3H, H-24), 1.72(t, J=7.14 Hz, 2H, H-5), 2.07(m, 2H, H-7), 2.33(t, J=6.9 Hz, 2 H, H-6), 3.55(t, J=6.64 Hz, 2H, H-21).

$^{13}$C-NMR(50 MHz, CDCl$_3$) δ: 11.4(C-24), 25.8(C-19), 26.8(C-22, 23), 28.8(C-8), 29.2-29.6(C-10 a C-18), 30.5(C-

7), 30.9(C-9), 32.7(C-20), 34.2(C-5), 36.2(C-4), 37.4(C-6), 62.8(C-21), 130.5(C-2), 165.6(C-3), 199.1(C-1).

Example 2

Synthesis of 3-(14-hydroxytetradecyl)-4-methyl-2-cyclohexen-1-one (1) Synthesis of 3-ethoxy-6-methyl-2-cyclohexen-1-one Diisopropylamine (3.4 mL, 24.4 mmol) dissolved in tetrahydrofuran (50 mL) was cooled to −78° C., n-butyllithium (8.2 mL, 12.3 mmol) was added thereto, and the temperature was elevated to 0° C. After having been stirred for 2 hours at 0° C., the reaction mixture was cooled to −78° C., and 3-ethoxy-2-cyclohexen-1-one (1.54 g, 11 mmol) dissolved in tetrahydrofuran (3 mL) was added thereto. After 2 hours of reaction, methyl iodide (0.77 mL, 12.4 mmol) was added, and the temperature of the reaction mixture was allowed to rise to room temperature. The reaction mixture was stirred for 18 hours at room temperature. Water (100 mL) was added thereto, and the resultant mixture was subjected to extraction three times with ethyl ether. The organic layers were combined, washed with an aqueous NaCl solution, dried over magnesium sulfate, filtered, and concentrated under reduced pressure. The crude product was purified by flash chromatography (ethyl ether/hexane=40/60), to thereby yield 1.19 g (7.7 mmol) of 3-ethoxy-6-methyl-2-cyclohexen-1-one.

Yield: 73%

$R_f$ (hexane/ethyl acetate=70/30)=0.41

$^1$H-NMR(200 MHz, CDCl$_3$) δ: 1.13(d, $^3$J=6.87 Hz, 3H, H-7), 1.33(t, $^3$J=7.01 Hz, 3H, OCH$_2$CH$_3$), 1.68(m, 1H, H-5), 2.03(m, 1H, H-5'), 2.26(m, 1H, H-6), 2.39(m, 2H, H-4), 3.85(q, $^3$J=7.04 Hz, 2H, OCH$_2$CH$_3$), 5.28(s, 1H, H-2).

$^{13}$C-NMR(50 MHz, CDCl$_3$) δ: 15.03(C-7), 16.28(OCH$_2$CH$_3$), 29.33(C-4), 30.18(C-5), 41.03(C-6), 65.06(OCH$_2$CH$_3$), 102.92(C-2), 177.75(C-3), 202.86(C-1).

(2) Synthesis of 3-(14-hydroxytetradecyl)-4-methyl-2-cyclohexen-1-one

14-Bromo-1-(t-butyldimethylsiloxy)tetradecane (1.814 g, 4.45 mmol) dissolved in absolute ethyl ether (4 mL) and magnesium (0.216 g, 8.9 mmol) were mixed, and dibromoethane was added dropwise to the resultant mixture, to thereby initiate Grignard reaction. The reaction was allowed to continue for 30 minutes. 3-Ethoxy-6-methyl-2-cyclohexen-1-one (0.825 g, 5.32 mmol) dissolved in tetrahydrofuran (4 mL) was added thereto. The mixture was stirred for 24 hours at room temperature. Subsequently, 10% hydrochloric acid (10 mL) was added for reaction under stirring for a further 24 hours. The reaction mixture was neutralized with saturated sodium hydrogencarbonate solution (10 mL) then subjected to extraction with ethyl ether (15 mL) three times. The organic layers were combined, washed with an aqueous NaCl solution, dried over magnesium sulfate, filtered, and concentrated under reduced pressure. The crude product was purified by means of flash chromatography (ethyl ether/hexane=70/30), to thereby yield 0.768 g (2.74 mmol) of 3-(14-hydroxytetradecyl)-4-methyl-2-cyclohexen-1-one.

Yield: 55%

$R_f$ (ethyl ether/hexane=70/30)=0.30

Melting point: 37-38° C.

$^1$H-NMR(200 MHz, CDCl$_3$) δ: 1.18(d, $^3$J=7.13 Hz, 3H, H-21), 1.25-1.59(m, 24H, H-8 to H-19), 1.69-1.84(m, 1H, H-5), 2.01-2.57(m, 6H, H-5'/H-7/H-6/H-7'/H-4/H-6'), 3.63 (t, $^3$J=6.50 Hz, 2H, H-20), 5.80(s, 1H, H-2).

$^{13}$C-NMR(50 MHz, CDCl$_3$) δ: 17.82(C-21), 25.76(C-5), 27.20-32.82(C-8 to C-19), 33.07(C-4), 34.23(C-7), 35.67(C-6), 63.07(C-20), 124.92(C-2), 170.72(C-3), 199.82(C-1).

INDUSTRIAL APPLICABILITY

The process of the present invention for producing cyclohexenone long-chain alcohol involves a reduced number of reaction steps, can be performed with ease at reduced production cost, and thus finds utility in the industry.

The invention claimed is:

1. A process for producing cyclohexenone long-chain alcohol represented by the following formula (1):

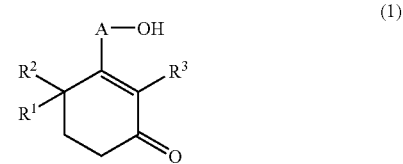

(wherein A represents a C10-C18 alkylene or alkenylene group, and each of $R^1$, $R^2$, and $R^3$ individually represents a hydrogen atom or a methyl group), comprising reacting a 3-alkoxy-2-cyclohexen-1-one derivative represented by the following formula (2):

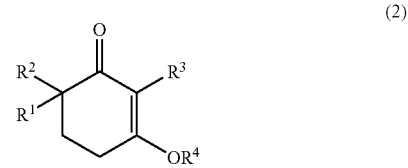

(wherein $R^1$, $R^2$, and $R^3$ have the same meanings as above, and $R^4$ represents a C1-C5 alkyl group) with a Grignard's reagent prepared from C10-C18 ω-halogenoalcohol whose hydroxyl group is protected through silylation, and hydrolyzing the resultant reaction product.

* * * * *